United States Patent

Behr et al.

[11] Patent Number: 5,442,081
[45] Date of Patent: Aug. 15, 1995

[54] PROCESS FOR THE PRODUCTION OF OLIGOMERIC FATTY ACIDS AND LOWER ALKYL ESTER THEREOF

[75] Inventors: Arno Behr; Hans-Peter Handwerk, both of Duesseldorf, Germany

[73] Assignee: Henkel Kommanditgesellschaft auf Aktien, Duesseldorf, Germany

[21] Appl. No.: 129,048

[22] PCT Filed: Mar. 26, 1992

[86] PCT No.: PCT/EP92/00676
§ 371 Date: Oct. 4, 1993
§ 102(e) Date: Oct. 4, 1993

[87] PCT Pub. No.: WO92/17434
PCT Pub. Date: Oct. 15, 1992

[30] Foreign Application Priority Data

Apr. 4, 1991 [DE] Germany .................. 41 10 836.1

[51] Int. Cl.⁶ .................................. C09F 7/06
[52] U.S. Cl. ........................ 554/26; 554/25; 554/167; 554/159
[58] Field of Search ............... 554/170, 25, 26, 167, 554/159

[56] References Cited

U.S. PATENT DOCUMENTS 3,341,570 9/1967 Barie ..................... 554/170
3,865,855 2/1975 Linn et al. .............. 260/413

FOREIGN PATENT DOCUMENTS 0842046 3/1955 Germany .

OTHER PUBLICATIONS

Rev. Fr. Corps. Gras. 33, 431 (1986).
Fette, Seifen, Anstrichmittel, 80, 186 (1978).
Römpp's Chemielexikon, 9th Ed., Thieme Verlag, Stuttgart, 1990 S.2322.
Fette, Seifen, Anstrichmittel, 72, 667 (1970).

*Primary Examiner*—José G. Dees
*Assistant Examiner*—Deborah D. Carr
*Attorney, Agent, or Firm*—Wayne C. Jaeschke; Norvell E. Wisdom, Jr.; Henry E. Millson, Jr.

[57] ABSTRACT

Process for the production of oligomeric fatty acids and lower alkyl esters thereof in which fatty acids containing 16 to 24 carbon atoms and 2, 3, 4 or 5 double bonds and/or lower alkyl esters thereof are oligomerized with $C_{1-4}$ alcohols at an elevated temperature in the presence of a tin halide catalyst, optionally in combination with a halide of titanium, iron, cobalt, nickel, lead, and/or germanium.

20 Claims, No Drawings

PROCESS FOR THE PRODUCTION OF OLIGOMERIC FATTY ACIDS AND LOWER ALKYL ESTER THEREOF

This application is a 371 of PCT/EP92/006761 filed Mar. 20, 1992.

BACKGROUND OF THE INVENTION

1. Field of the Invention

This invention relates to a process for the production of oligomeric fatty acids and lower alkyl esters thereof by oligomerization of fatty acids or lower alkyl esters thereof in the presence of Lewis acids.

2. Statement of Related Art

Oligomeric fatty acids and their esters, i.e. technical mixtures of acyclic and cyclic di-, tri- and oligocarboxylic acids or esters, are important products which are used for the production of adhesives, paints, fibers, corrosion inhibitors and lubricants.

Among the oligomeric fatty acids, the dimer fatty acids are particularly important. They are normally obtained by oligomerization of unsaturated fatty acids at temperatures of 180° to 250° C. in the presence of aluminas, for example montmorillonites (Fette, Seifen, Anstrichmittel, 72, 667 (1970)). However, the process is attended by the disadvantage that achieving satisfactory oligomerization yields requires not only comparatively high catalyst concentrations, but also drastic reaction conditions which involve high energy consumption.

It is known from Rev. Fr. Corps. Gras, 33, 431 (1986) that the oligomerization of linoleic acid can also be carried out in the presence of ruthenium or nickel on active carbon supports. Although the process manages with low catalyst concentrations, high yields of oligomers are only obtained at temperatures above 200° C.

Finally, it is reported in Fette, Seifen, Anstrichmittel, S80, 186 (1978) that linoleic acid esters can be quantitatively oligomerized at only 80° C. in the presence of rhodium/olefin complexes and tin(II) chloride. This process has the disadvantage that the production of rhodium/olefin complexes involves significant outlay on equipment. In addition, the use of homogeneous rhodium catalysts is economically unfavorable.

DESCRIPTION OF THE INVENTION

Accordingly, the problem addressed by the present invention was to provide a new process for the oligomerization of fatty acids or fatty acid esters which would not have any of the disadvantages mentioned above.

The present invention relates to a process for the production of oligomeric fatty acids and lower alkyl esters thereof, characterized in that fatty acids containing 16 to 24 carbon atoms and 2, 3, 4 or 5 double bonds or lower alkyl esters thereof are oligomerized with $C_{1-4}$ alcohols at elevated temperature in the presence of at least one Lewis acid.

It has surprisingly been found that the oligomerization of unsaturated fatty acids and lower alkyl esters thereof does not require the presence of noble metals or their complexes, but instead takes place with satisfactory oligomer yields and selectivities under comparatively mild conditions, even in the presence of readily obtainable Lewis acids. Accordingly, the process according to the invention represents a clear advance over the prior art both in terms of handling and in terms of profitability.

Suitable starting materials for the oligomerization are fatty acids containing 16 to 24 carbon atoms and 2, 3, 4 or 5 double bonds and lower alkyl esters thereof. Typical examples are linoleic acid, linolenic acid, arachidonic acid or clupanodonic acid and, for example, methyl esters thereof. The corresponding conjuene fatty acids, which are obtained from the fatty acids mentioned by isomerization of the double bonds in the presence of alkali (Römpp's Chemielexikon, 9th Edition, Thieme Verlag, Stuttgart, 1990, page 2322) may also be used in the oligomerization reaction. The term "conjuenes" is jargon for multiple unsaturated organic compounds whose double-bonds remain in conjugation. Examples: diene, triene, polyene. Accordingly those fatty acids combine as conjuene fatty acids, whose double-bonds (e.g. linoleic-, linolenic-, arachidonic-, clupanodonic acid) are conjugated under alkali influence. Linoleic acid, conjuene fatty acid based on linoleic acid and methyl esters thereof are preferably used.

As usual in oleochemistry, the fatty acids mentioned or their lower alkyl esters may also be present in the form of the technical mixtures formed in the pressure hydrolysis or transesterification of fats and oils, for example soybean oil, sunflower oil, linseed oil or fish oil. Technical fatty acids and fatty acid ester fractions which, in addition to the saturated and monounsaturated fatty acids, contain the polyunsaturated fatty acids mentioned to a predominant extent, i.e. in a proportion of more than 50% by weight, may also be used for oligomerization by the process according to the invention.

Suitable Lewis acids are the halides, particularly the chlorides, of the elements of the 3rd and 4th main group and 4th and 8th secondary group of the periodic system of elements. Typical examples are boron trifluoride, aluminium trichloride, germanium tetrachloride, tin dichloride, tin tetrachloride, lead dichloride, titanium tetrachloride, iron dichloride, iron trichloride, cobalt dichloride or nickel dichloride. Tin halides, particularly chlorides of tin in its oxidation stages $+II$ and $+IV$, are preferably used. In a particularly preferred embodiment, tin tetrachloride is used for the specific production of trimeric fatty acids or lower alkyl esters thereof. The Lewis acids may be used in dehydrated form, but are preferably used in the form of salts containing water of crystallization. Where boron trifluoride is used, it is advisable to employ the diethyl ether complex.

The Lewis acids may be used individually, although it has proved to be of particular advantage to use mixtures of at least two Lewis acids, one of which is a tin halide, because combinations such as these can have synergistic effects on the yield and selectivity of oligomers.

The Lewis acids may be used in total quantities of 0.1 to 10 mol-% and preferably in total quantities of 1 to 8 mol-%, based on the fatty acids or the fatty acid esters. Where mixtures of different Lewis acids are used, their molar ratio to one another is not critical. However, mixtures of two Lewis acids which contain the components in a molar ratio of 5:1 to 1:5 and preferably 4:1 are preferred. Optimal oligomerization results are obtained when the tin halide is present in excess in the binary mixtures in question.

The oligomerization may be carried out by initially introducing the fatty acids or fatty acid esters, Lewis acids and, optionally, an organic solvent, for example chloroform, into a pressure vessel and, after closing the autoclave, reacting the reaction mixture for 0.5 to 24 h and preferably for 5 to 20 h at a temperature of 60° to 150° C. and preferably at a temperature of 80° to 120° C. under the autogenous pressure established of 2 to 5 bar.

The oligomeric fatty acids or their lower alkyl esters are obtained in the form of colorless to pale yellow liquids after separation of the catalyst, for example by adsorption to active carbon, silica gel or aluminium oxide, and contain dimeric, trimeric and higher acyclic and cyclic products, of which the degree of oligomerization can be determined by gel permeation chromatography, in addition to unreacted starting ester optionally structurally isomerized in the alkyl chain. The products are particularly suitable for the production of lubricants, fibers and adhesives.

The following Examples are intended to illustrate the invention without limiting it in any way.

EXAMPLES

Examples 1 to 16, Comparison Example C1:

General procedure for the oligomerization of fatty acid esters.

6.2 g (19 mmol) conjuene fatty acid methyl based on linoleic fatty acid methyl ester were introduced into an argon-purged stirred glass autoclave and, after addition of the catalyst and 20 ml chloroform, were heated for 20 h to 100° C. After cooling, the catalyst was separated by adsorption to silica gel and the solvent was removed in a rotary evaporator. The resulting fatty acid ester mixture was analyzed by gel permeation chromatography. Particulars of the catalyst, the quantities of catalyst used and the composition of the reaction products are shown in Table 1 below.

B) isolating an oligomeric fatty acid and/or lower alkyl ester thereof from the reaction mixture.

2. The process of claim 1 wherein in step A) the at least one fatty acid and/or lower alkyl ester thereof is either linoleic acid, conjuene acid based on linoleic acid, or a methyl ester of one of the foregoing.

3. The process of claim 1 wherein in step A) the catalyst is present in from 0.1 to 10 mol %, based on the at least one fatty acid and/or ester thereof.

4. The process of claim 1 wherein step A) is carried out at a temperature of from 60° to 150° C.

5. The process of claim 1 wherein in step A) the catalyst is $SnCl_2$.

6. The process of claim 1 wherein in step A) the catalyst is $SnCl_4$.

7. The process of claim 1 wherein in step A) the at least one fatty acid and/or ester thereof is a fatty acid or ester mixture from the pressure hydrolysis or transesterification of a fat or oil.

8. The process of claim 7 wherein said fat or oil is soybean oil, sunflower oil, linseed oil, or fish oil.

9. The process of claim 1 wherein step A) is carried out at a temperature of from 80° to 120° C. and at a pressure of from 2 to 5 bar.

10. The process of claim 1 wherein step B) is carried out by separating the catalyst from the reaction product by adsorption of the catalyst on active carbon, silica gel, or aluminum oxide.

11. The process of claim 1 wherein in step A) the catalyst is present in from 0.1 to 10 mol %, based on the at least one fatty acid and/or ester thereof, step A) is carried out at a temperature of from 60° to 150° C., and step B) is carried out by separating the catalyst from the reaction product by adsorption of the catalyst on active carbon, silica gel, or aluminum oxide.

12. The process of claim 11 wherein in step A) the tin halide is either $SnCl_2$ or $SnCl_4$.

13. The process of claim 12 wherein step A) is carried out at a temperature of from 80° to 120° C. and at a pressure of from 2 to 5 bar, and the catalyst is present in from 1 to 8 mol %.

TABLE 1

Oligomerization tests Percentages are % by weight

| Ex. | LA A | c(LA A) mmol | LA B | c(LA B) mmol | Yield % | Oligomer distribution Dim. % | Trim. % | Higher O. % |
|---|---|---|---|---|---|---|---|---|
| 1 | $SnCl_2$ | 1.5 | — | — | 45 | 22 | 17 | 6 |
| 2 | $SnCl_4$ | 1.5 | — | — | 70 | 19 | 29 | 22 |
| 3 | $FeCl_3$ | 0.4 | — | — | 50 | 18 | 17 | 15 |
| 4 | $FeCl_3$ | 0.4 | $SnCl_4$ | 1.5 | 73 | 16 | 28 | 28 |
| 5 | $FeCl_3$ | 0.4 | $SnCl_2$ | 1.5 | 67 | 20 | 28 | 19 |
| 6 | $TiCl_4$ | 0.4 | — | — | 57 | 20 | 23 | 15 |
| 7 | $TiCl_4$ | 0.4 | $SnCl_2$ | 1.5 | 73 | 16 | 37 | 20 |
| 8 | $BF_3$* | 0.4 | — | — | 61 | 24 | 24 | 13 |
| 9 | $NiCl_2$ | 0.4 | $SnCl_2$ | 1.5 | 69 | 20 | 30 | 19 |
| 10 | $NiCl_2$ | 0.4 | $SnCl_4$ | 1.5 | 71 | 20 | 31 | 19 |
| 11 | $CoCl_2$ | 0.4 | $SnCl_2$ | 1.5 | 63 | 22 | 26 | 15 |
| 12 | $CoCl_2$ | 0.4 | $SnCl_4$ | 1.5 | 72 | 20 | 32 | 20 |
| 13 | $PbCl_2$ | 0.4 | $SnCl_2$ | 1.5 | 67 | 20 | 27 | 20 |
| 14 | $GeCl_4$ | 0.4 | $SnCl_2$ | 1.5 | 70 | 21 | 34 | 16 |
| 15 | $AlCl_3$ | 0.4 | $SnCl_2$ | 1.5 | 68 | 21 | 29 | 19 |
| 16 | $AlCl_3$ | 0.4 | $SnCl_4$ | 1.5 | 70 | 20 | 32 | 19 |
| C1 | No catalyst | | | | 18 | 13 | 3 | 2 |

Legend:
LA = Lewis acid
c(LA) = Concentration of the Lewis acid
Yield = Total yield of oligomers
Dim. = Percentage dimer content
Trim. = Percentage trimer content
Higher O. = Percentage content of higher oligomers
*Boron trifluoride used in the form of a 50% by weight solution of the diethyl ether complex.

We claim:

1. A process for the production of oligomeric fatty acids and/or lower alkyl esters thereof comprising the steps of
A) oligomerizing at least one fatty acid containing 16 to 24 carbon atoms and 2, 3, 4 or 5 double bonds and/or a lower alkyl ester thereof with a $C_{1-4}$ alcohol at an elevated temperature in the presence of a catalyst comprising an inorganic tin halide; and 14. The process of claim 12 wherein in step A) the at least one fatty acid and/or lower alkyl ester thereof is either linoleic acid, conjuene acid based on linoleic acid, or a methyl ester of one of the foregoing.

15. A process for the production of oligomeric fatty acids and/or lower alkyl esters thereof comprising the steps of
   A) oligomerizing at least one fatty acid containing 16 to 24 carbon atoms and 2, 3, 4 or 5 double bonds and/or a lower alkyl ester thereof with a $C_{1-4}$ alcohol at an elevated temperature in the presence of a catalyst comprising a tin halide and at least one halide of titanium, iron, cobalt, nickel, lead, and/or germanium; and
   B) isolating an oligomeric fatty acid and/or lower alkyl ester thereof from the reaction mixture.

16. The process of claim 15 wherein in step A) the catalyst is present in from 0.1 to 10 mol %, based on the at least one fatty acid and/or ester thereof.

17. The process of claim 15 wherein in step A) the tin halide component of the catalyst is $SnCl_2$.

18. The process of claim 15 wherein in step A) the tin halide component of the catalyst is $SnCl_4$.

19. The process of claim 16 wherein said mol % is from 1 to 8 mol %.

20. The process of claim 15 wherein in the catalyst the tin halide is present in excess.

* * * * *